(12) United States Patent  
Benett et al.

(10) Patent No.: US 6,699,713 B2
(45) Date of Patent: Mar. 2, 2004

(54) POLYMERASE CHAIN REACTION SYSTEM

(75) Inventors: William J. Benett, Livermore, CA (US); James B. Richards, Danville, CA (US); Paul L. Stratton, Brentwood, CA (US); Dean R. Hadley, Manteca, CA (US); Fred P. Milanovich, Lafayette, CA (US); Phil Belgrader, Manteca, CA (US); Peter L. Meyer, Somerset, CA (US)

(73) Assignee: The Regents of the University of California, Oakland, CA (US)

( * ) Notice: Subject to any disclaimer, the term of this patent is extended or adjusted under 35 U.S.C. 154(b) by 233 days.

(21) Appl. No.: 09/752,794

(22) Filed: Dec. 29, 2000

(65) Prior Publication Data

US 2002/0191826 A1 Dec. 19, 2002

Related U.S. Application Data

(60) Provisional application No. 60/174,416, filed on Jan. 4, 2000.

(51) Int. Cl.[7] .................................... C12M 1/34
(52) U.S. Cl. .................... 435/287.2; 435/303.1; 435/285.1; 356/417
(58) Field of Search .................... 356/417, 317, 356/318; 250/458.1, 459.1, 461.1, 461.2; 422/82.08, 82.07, 58, 82.05, 82.09, 102, 129, 240, 241, 131; 436/172, 514–518; 435/285.1, 292.1; 935/88

(56) References Cited

U.S. PATENT DOCUMENTS

| 5,589,136 A | 12/1996 | Northrup et al. ........... 422/102 |
| 5,721,123 A | 2/1998 | Hayes et al. ............... 435/91.1 |
| 5,965,410 A | 10/1999 | Chow et al. ............... 435/91.2 |
| 6,369,893 B1 * | 4/2002 | Christel et al. ............ 356/417 |

FOREIGN PATENT DOCUMENTS

| WO | WO98/43740 | 10/1998 |
| WO | WO99/12016 | 3/1999 |
| WO | WO99/48608 | 9/1999 |

OTHER PUBLICATIONS

W.J. Benett, et al., "Handheld Advanced Nucleic Acid Analyzer," UCRL–JC–136587, Preprint, U.S. Dept. of Energy, Lawrence Livermore National Laboratory, Oct. 6, 2000, 11 pages.

James B. Richards, et al., "Miniaturized Detection System for Handheld PCR Assays," UCRL–JC–138399 Preprint, U.S. Dept. of Energy, Lawrence Livermore National Laboratory, Oct. 6, 2000, 12 pages.

* cited by examiner

Primary Examiner—Ethan Whisendnt
Assistant Examiner—Shar Hashemi
(74) Attorney, Agent, or Firm—Eddie E. Scott; Alan H. Thompson

(57) ABSTRACT

A portable polymerase chain reaction DNA amplification and detection system includes one or more chamber modules. Each module supports a duplex assay of a biological sample. Each module has two parallel interrogation ports with a linear optical system. The system is capable of being handheld.

40 Claims, 7 Drawing Sheets

Figure 1. HANAA "Handheld Advanced Nucleic Acid Analyzer"

Micromachined silicon PCR heater chamber. Thickness is 2.0 mm.

Standard assay configuration for the HANAA. The upper channel is used for a positive internal control.

14A

HANAA chamber module with filter holders removed.

Sketch showing HANAA optical paths. The crosshatched rectangles indicate filter positions.

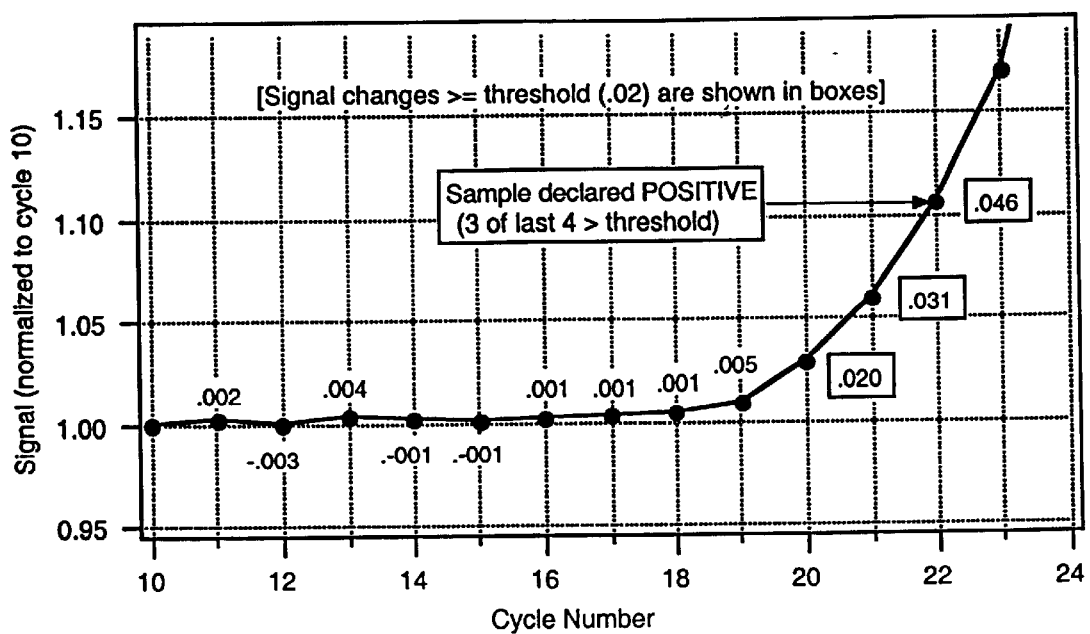
Fig. 7. Graphical depiction of positive calling algorithm used in the HANAA.

US 6,699,713 B2

POLYMERASE CHAIN REACTION SYSTEM

CROSS-REFERENCE TO RELATED APPLICATIONS

This application claims the benefit of U.S. Provisional Application No. 60/174,416 filed Jan. 04, 2000, entitled "Handheld PCR instrument," which is incorporated herein by this reference.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to instruments for chemical reaction, amplification, and detection, and in particular, to a system for doing polymerase chain reaction, amplification, and detection.

2. State of Technology

U. S. Pat. No. 5,589,136 for silicon-based sleeve devices for chemical reactions, by Northrup et al, patented Dec. 31, 1996, provides the following description: "A silicon-based sleeve type chemical reaction chamber that combines heaters, such as doped polysilicon for heating, and bulk silicon for convection cooling. The reaction chamber combines a critical ratio of silicon and silicon nitride to the volume of material to be heated (e.g., a liquid) in order to provide uniform heating, yet low power requirements. The reaction chamber will also allow the introduction of a secondary tube (e.g., plastic) into the reaction sleeve that contains the reaction mixture thereby alleviating any potential materials incompatibility issues. The reaction chamber may be utilized in any chemical reaction system for synthesis or processing of organic, inorganic, or biochemical reactions, such as the polymerase chain reaction (PCR) and/or other DNA reactions, such as the ligase chain reaction, which are examples of a synthetic, thermal-cycling-based reaction. The reaction chamber may also be used in synthesis instruments, particularly those for DNA amplification and synthesis."

A paper titled "Handheld advanced Nucleic Acid Analyzer" was presented by W. J. Benett, J. B. Richards, P. Stratton, D. R. Hadley, B. H. Bodtker, S. L. Nasarabadi, F. P. Milanovich, R. P. Mariella, R. P. Koopman, and P. Belgrader at the Society of Photo-Optical Instrumentation Engineers Symposium on Environmental and Industrial Sensing, Boston, Mass. Nov. 5–8, 2000. This paper is incorporated herein by reference.

A paper titled "Miniaturized detection system for handheld PCR assays" was presented by J. B. Richards, W. J. Benett, P. Stratton, D. R. Hadley, S. L. Nasarabadi, and F. P. Milanovich, at the Society of Photo-Optical Instrumentation Engineers Symposium on Environmental and Industrial Sensing, Boston, Mass. Nov. 5–8, 2000. This paper is incorporated herein by reference.

SUMMARY OF THE INVENTION

The present invention provides a polymerase chain reaction DNA amplification and detection system. An embodiment of the system includes one or more sample chamber modules adapted to contain biological sample volumes. Each of the sample chamber modules has the ability to support a duplex assay and has parallel interrogation ports operatively connected to the chamber modules. Each of the ports has an optical fluorescence detection system. Additional aspects, advantages, and features of the invention are set forth in part in the following description. Various aspects, advantages, and features of the invention will become apparent to those skilled in the art upon examination of the description and by practice of the invention.

BRIEF DESCRIPTION OF THE DRAWINGS

The accompanying drawings, which are incorporated into and form a part of the disclosure, illustrate embodiments of the invention, and, together with the description, serve to explain the principles of the invention.

FIG. 7 is a graphical depiction of positive calling algorithm used in the HANAA.

DETAILED DESCRIPTION OF THE INVENTION

The detailed description of the various embodiments, together with the general description of the invention, serves to explain the principles of the invention. One embodiment of the invention provides a polymerase chain reaction DNA amplification and detection system having a main body and one or more sample chamber modules adapted to contain biological sample volumes. Each of the sample chamber modules has the ability to support a duplex assay. Parallel interrogation ports are operatively connected to the sample chamber modules. Another embodiment of the polymerase chain reaction DNA amplification and detection includes a linear detection system operatively connected to individual interrogation ports. Sample chamber modules have multiple interrogation ports that interrogate distinct regions within the sample volume. Each parallel interrogation port has its own optical fluorescence detection system. Another embodiment of the system includes LEDs that direct light energy into the parallel interrogation ports. Another embodiment of the polymerase chain reaction DNA amplification and detection system includes a positive calling algorithm. In the various embodiments of the system a sample is place in at least one of a multiplicity of sample chamber modules. The sample is heated using a heating unit in a silicon base and the sample is cooled. Light energy is directed into the sample through the parallel interrogation ports and characteristics of the sample are detected.

Overview

The polymerase chain reaction (PCR) is widely accepted as the gold standard for identification of biological organisms. PCR is a biochemical method by which the concentration of DNA segments in solution is increased at an exponential rate over time. It is capable of distinguishing between strains of organisms of the same species. PCR typically requires a sample to be repeatedly cycled between temperatures near 95° C. and a temperature below 60° C. Theoretically, the concentration of the DNA segments doubles each cycle. The present invention provides various embodiments of systems for doing polymerase chain reaction (PCR) amplification and detection. The systems are lightweight, compact, and power efficient.

The Handheld Advanced Nucleic Acid Analyzer (HANAA)

Figure 1:
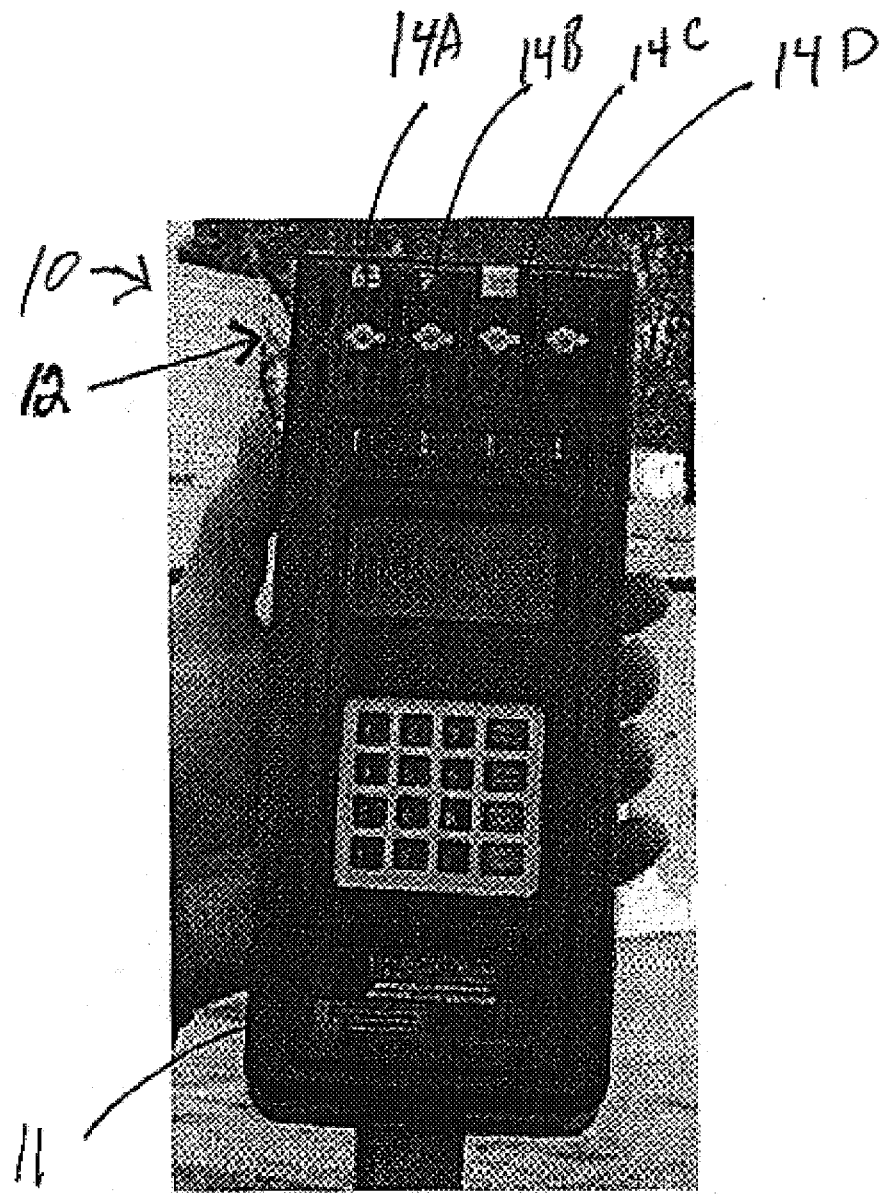
FIG. 1 illustrates an embodiment of the present invention.

Referring now to the drawings, and in particular to FIG. 1, an embodiment of the present invention is illustrated. The system 10 is referred to as the "HANAA" (Handheld Advanced Nucleic Acid Analyzer). The system 10 is a four chamber, battery powered, handheld instrument. The system 10 consists of two basic component parts 11 and 12. One component is the main body 11 of which contains the electronics (including detectors), batteries, and the operator interface. The second component is the sample module 12. The sample module 12 slides into a docking system on the end of the main body 11. The instrument size is approximately 10 inches long×4 inches wide×2 inches deep. Additional details of the HANAA system 10 will be described subsequently.

The HANAA embodiment is designed to be used at any desired location including use by military or law enforcement personnel. It is also suited for use by medical personnel in a clinic setting. Applications for the HANAA include detection of any DNA or RNA based organisms or samples from such organisms. Examples include pathology, forensics, detection of biological warfare agents, infectious disease diagnostics, genetic testing, and environmental testing. The HANAA embodiment of the present invention includes four chamber modules, 14A, 14B, 14C, and 14D which are thermally cycled simultaneously or independently. This allows for positive and negative controls and varying sample concentrations. Each of the four chamber modules has the ability to support a duplex assay for two independent measurements on one sample. The thermal cycler structure allows for two parallel interrogation ports while retaining an extremely small mechanical profile. Each port has a unique, specialized optical detection system that retains the compact planar geometry of the chamber module. The output of the detection system is analyzed by an algorithm that automatically determines when a sample is positive while displaying assay information in real time in a unique, versatile format.

The HANAA includes sample modules, which incorporate an advanced silicon thermal cycler. An advanced silicon thermal cycler is shown in U.S. Pat. No. 5,589,136, titled "Silicon-Based Sleeve Devices for Chemical Reactions, patented Dec. 31, 1996 by Northrup et al, assigned to the same assignee. The specification and drawings of U.S. Pat. No. 5,589,136 are incorporated herein by this reference. The HANAA thermal cycler design has an anisotropically etched architecture that reduces thermal mass and increases cooling efficiency. This combined with a thin film heater/temperature sensor enables extremely rapid and efficient thermal cycling. The HANAA thermal cycler has two windows, allowing for two independent optical paths for excitation and detection while retaining an extremely small mechanical profile. Each port has its own light emitting diode—(LED) and an extremely simple and straightforward optical system, which lowers complexity, size and cost while increasing reliability and performance.

The HANAA monitors the polymerase chain reaction (PCR) process using a TaqMan® based fluorescence assay with optical probes included in the sample solution. The PCR procedure involves: 1) processing of the sample to release target DNA molecules into a crude extract; 2) addition of an aqueous solution containing enzymes, buffers, deoxyribonucleotide triphosphates (dNTPS), and oligo- nucleotide primers; 3) thermal cycling of the reaction mixture between two or three temperatures (e.g., 90°–96°, 72°, and 37°–55° C.); and 4) detection of amplified DNA. Intermediate steps, such as purification of the reaction products and the incorporation of surface-bending primers, for example, may be incorporated in the PCR procedure.

Real-time optical detection of the PCR concentration is possible when optical probes are included in the sample solution. The probes, for example, may be TaqMan® probes available from Applied Biosystems, a business unit of PE Corporation, 761 Main Avenue, Norwalk, Conn. 06859-0001. These TaqMan® probes contain a dye molecule that is initially quenched by Forster energy transfer. During the replication process, an enzyme (Taq polymerase) chews apart the probe complex. This separates the dye from the quencher, at which point the reporter dye can emit its characteristic fluorescence. Real-time detection reduces assay time as a sample need not cycle to completion to detect a positive. Also, follow-on processing steps such as gel electrophoresis are not required. Real-time detection is provided without sacrificing cycling speed or significantly increasing size or power consumption. This embodiment of the present invention provides a versatile hand held PCR thermal-cycler with real time detection.

Controlling the HANAA Heater

Figure 2:
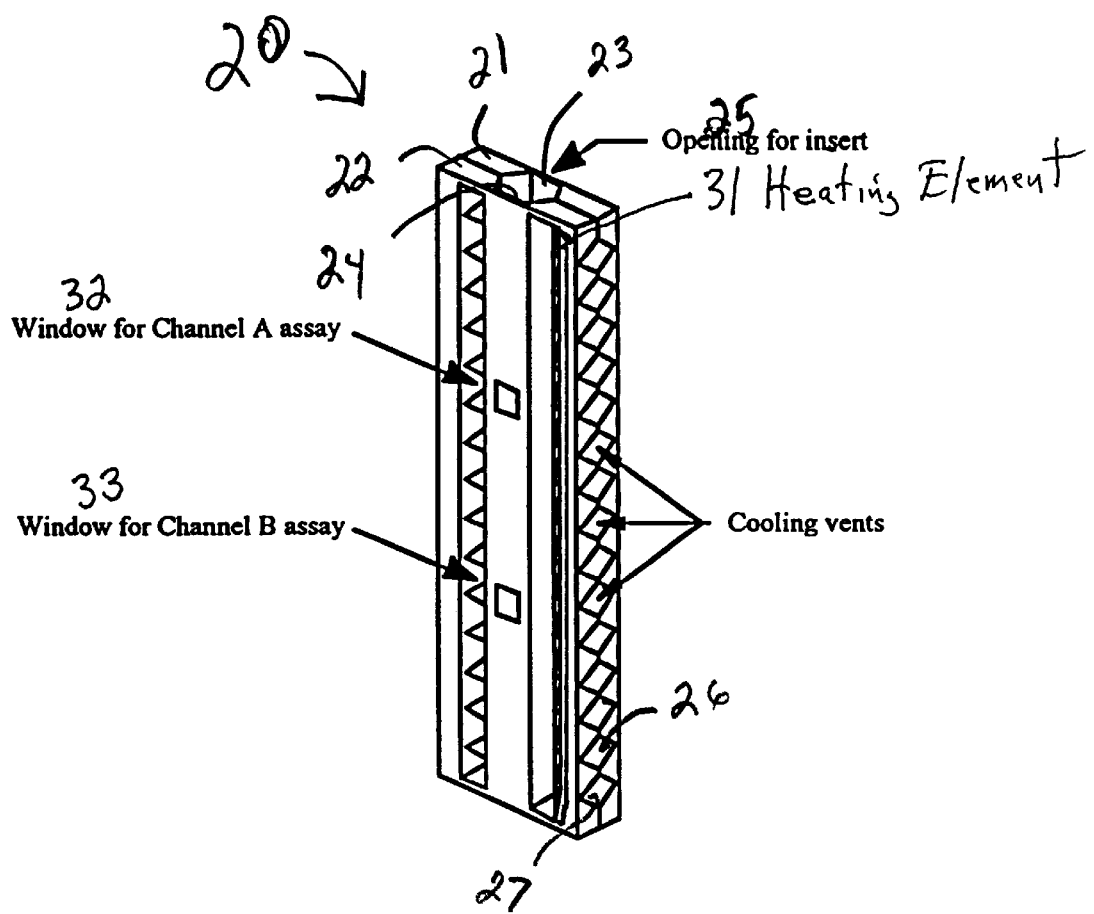
FIG. 2 is an isometric view of a micromachined silicon PCR heater chamber.
Figure 3:
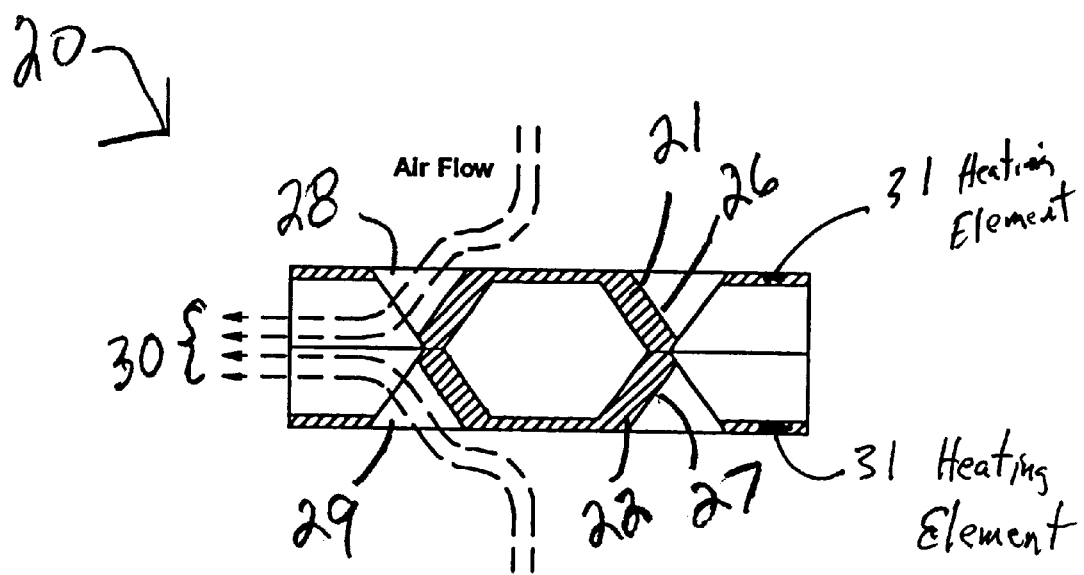
FIG. 3 is cross-sectional view showing air cooling of the PCR heater chamber.

As illustrated in FIGS. 2 and 3, the HANAA heater and sleeve reaction chamber is generally indicated at 20. Sleeve-type reaction chambers are shown in U.S. Pat. No. 5,589,136 issued Dec. 31, 1996, as well as copending U.S. application Ser. No. 09/200,309, filed Nov. 25, 1998, entitled "An Improved PCR Thermocycler," each assigned to the same assignee. The disclosures of U.S. Pat. No. 5,589,136 and copending U.S. patent application Ser. No. 09/200,309, filed Nov. 25, 1998 are incorporated herein by reference, The HANAA heater and sleeve reaction chamber 20 is composed of two silicon body members or sections 21 and 22. Each of the body members 21 and 22 have longitudinally extending cutaway 23 and 24 along the entire length thereof which form a opening for an insert 25 (also referred to as a reaction chamber 25) when the body sections 21 and 22 are secured together. Longitudinally extending, spaced, V-shaped grooves 26 and 27 are formed in the external faces or sides of each of the body sections 21 and 22. The V-shaped grooves 26 and 27 are formed on the inner surfaces of the outer sides of body sections 21 and 22, as illustrated in FIGS. 1A and 1B. The V-shaped longitudinally extending grooves 26 and 27 form air flow passageways 28 and 29 as indicated by the arrows 30.

As the air flows through the passageways formed by the interconnected grooves 26 and 27 that form passageways 28 and 29, it removes heat from the surfaces of chamber 25, thereby increasing the speed and efficiency of the sleeve reactor chamber or PCR thermal cycler 20. By reduction of the thermal mass of the body sections 21 and 22 and the increase in the surface areas thereof, improved thermal performance is provided.

The grooves 26 and 27 and passageways 28 and 29 are anisotropically etched into the silicon wafers during the formation of the body sections or members 21 and 22. After etching the body members 21 and 22 to form the cutaways 23 and 24, which define the reaction chamber 25, and etching the body members to form the longitudinal extending grooves 26 and 27 which form air flow passageways 28 and 29, the body members 21 and 22 are secured together, such as by bonding, gluing, spring loading, etc.

A heater strip 31 provides the central heating element. The heater strip 31 is constructed from platinum and operates as a resistance heater. Because of platinum's relatively high temperature coefficient of resistance the heater 31 is also used as a temperature sensor. This enables more accurate thermal control and greatly simplifies the overall design.

Thermal profiles (temperature versus time) are most efficient when the transition time between high and low temperatures is minimized. This can be done by having rapid heating and cooling rates. In addition, the "corners" of the profile, where the rapid rate stops and the heater maintains a fixed (hold) setpoint temperature, need to be as sharp as possible. The HANAA achieves this by overheating the chamber during the heating cycle (and overcooling during the cooling cycle). The heater current is instantly dropped to the simmer level when the liquid is very close to the desired hold temperature. With a low mass chamber, there is virtually no overshoot of temperature beyond when the current is reduced. This leads to a very sharp knee when compared to conventional methods, which either lower the heating rate as the temperature nears the setpoint, overshoot the setpoint due to temperature oscillations or react so slowly that such a method is not applicable in the first place.

Cooling the chamber requires blowers and a ducting system that pull air in from outside the instrument, circulate it as close to the heated surfaces as possible, then redirect it out of the chamber and back to the outside. Air enters through two plenums at the top of the dividing walls on either side of the module. It is directed through apertures in the walls that line up with the array of cooling ports on the chamber, then exits the chamber through apertures in the walls, mid-way between the input apertures. From that point, the air is pulled into the plenum below the module, into the blowers, into the main body, then out vents in the side of the main housing.

HANAA Assay Configuration

Figure 4:
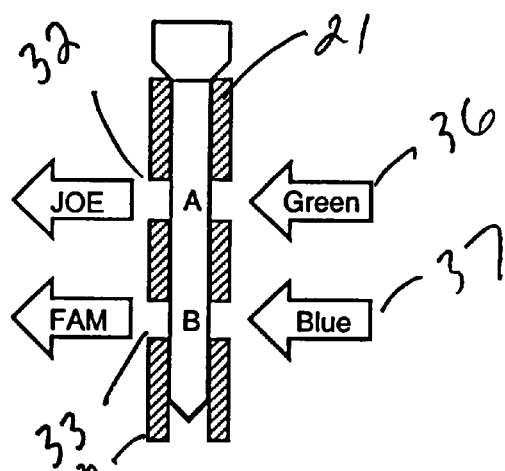
FIG. 4 shows a standard assay configuration for the HANAA with the upper channel used for a positive internal control.
Figure 5:
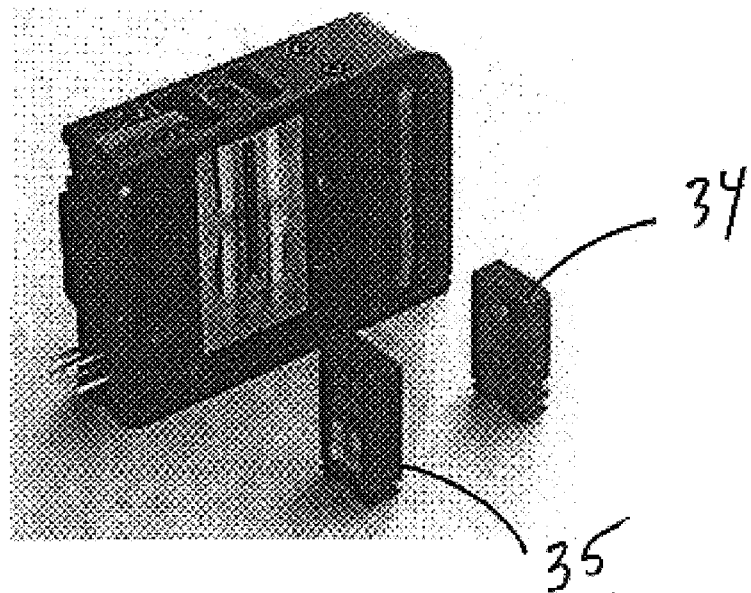
FIG. 5 shows a HANAA chamber module with the filter holders removed.

Each chamber uses two detection wavelengths. Given the long, narrow sample containers and the versatility of silicon, the HANAA provides the option of having two, physically separate windows 32 and 33 shown best in FIG. 4 through which to probe the sample. This provides a major benefit in that it simplifies the system by reducing it to two parallel, linear optical paths. This eliminates the need for any beam splitters or dichroic filters while drastically reducing the package size. FIG. 5 shows one of the sample modules 14A with filter holders 34 and 35 removed.

HANAA Optical System

Figure 6:
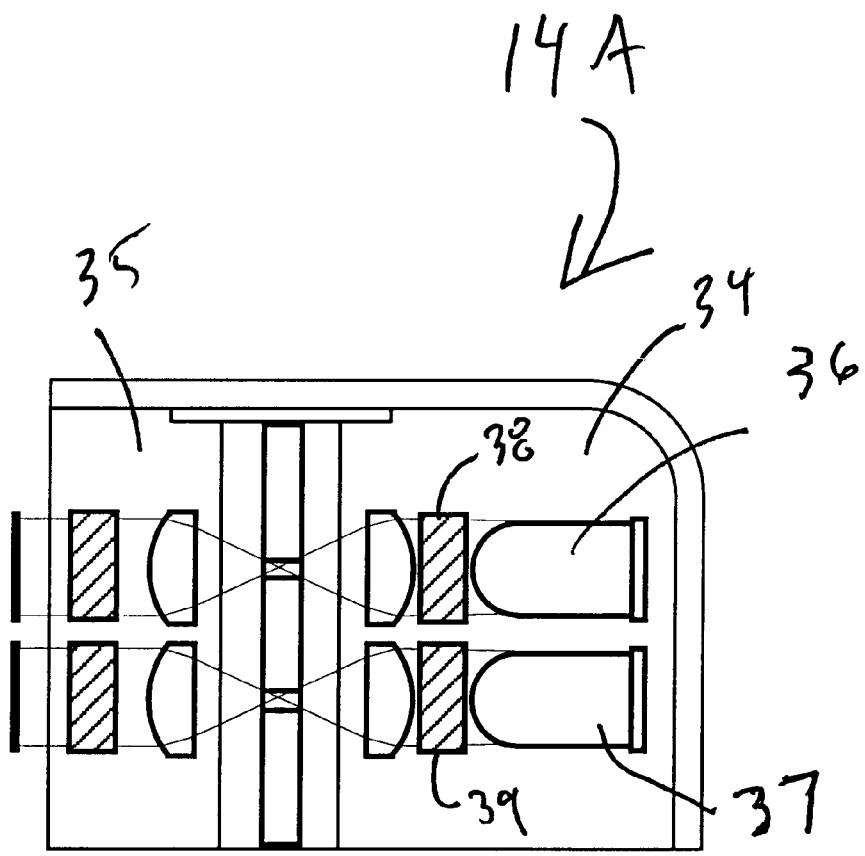
FIG. 6 is a sketch showing HANAA optical paths.

The optical system is shown in FIG. 6, where the light travels from right to left along two parallel paths. LEDs 36 and 37 meet the size, power consumption and cost criteria for the HANAA. Standard 5 mm LED packages are used based on availability and relatively low divergence angles. The blue LED 37 has a very low divergence half angle of 10 degrees. Given the extremely short optical path, the forgiving focusing requirement, and the large aperture throughout the module, this divergence works well. The green LED 36 is specified to be 15 degrees divergence, which is significantly more, but still narrow enough for the HANAA system to preclude the need for a collimating lens prior to the bandpass clean up filter.

Bandpass filters 38 and 39 are needed in front of the LEDs to filter out the long wavelength shoulders of the LED spectra. These wavelengths directly overlay the emission wavelengths and therefore must be highly attenuated. Given the diverging optical beams from the LEDs, light impinges on the filters over a range of angles, resulting in a shift in transmission to lower wavelengths. In general, all filters within the HANAA chamber modules have been specified conservatively to allow for the effect of this tilt factor. In particular, the emission filters have band edges with a bit longer wavelength than normal to allow for the transmission of shorter wavelengths incident over a shallow cone of angles. The interference excitation filter is backed up by absorbing glass to eliminate long wavelength radiation beyond the emission band.

The window apertures 32 and 33 in the silicon chambers are relatively large (1.4 by 1.4 mm). As such, the focusing requirements of the LED lenses are minimal and standard plano-convex lenses can be used. The excited volume for the sample inside each window is approximately one cubic millimeter.

Light exiting the heater chamber, both excitation and emission, is collected by another plano-convex lens, which essentially recollimates the light. Since all emitted light occurs within approximately 0.5 mm of the lens focal point, collection efficiency is extremely efficient. The solid angle of collection is essentially the same for the entire excited volume and the entire sampled volume is uniformly excited. Since there is no way to separate the excitation light from the detection path without significantly increasing the size of the sample module, the emission filter must effectively reject the excitation light in order to make a reliable measurement. In practice, the filters perform quite well. Any leakage from the excitation source to the detector appears as a constant signal. Signal increases due to increased PCR product appear on top of any leakage. The result is that there is no decrease in signal-to-noise ratio due to leakage.

Mechanical measures are also employed to limit the angle of incidence on the emission filters. In the region between the collimating lens and filter, there is a 4 mm optical path with internal baffles. A fused deposition modeling machine was used to form the baffling structure out of black ABS plastic. The optical channel is essentially 4 mm in diameter with the sides being a series of 4 annular, sawtoothed grooves that trap divergent light to keep it from deflecting off the wall and back onto the filter.

Standard silicon photodiodes are used for detection, followed by a charge integration circuit. The integration time can be varied depending on the assay. In the case of the HANAA, there are two separate excitation sources interrogating two different volumes within the sample at slightly different times. Since the HANAA's LED sources are separated in wavelength, the emission bands can be separated further in wavelength than in a single source instrument, resulting in less emission being collected by the neighboring detector.

Ultimately, it is not just the wavelength separation between the sources but the temporal separation that is the key to discriminating signals on the HANAA. When the positive assay s LED is illuminated, the detector circuit for the negative assay is turned off. Thus, when the negative assay is interrogated, its LED is far less efficient at exciting the positive assays fluorophore. The combination of inefficient excitation and inefficient collection of emission enables the HANAA to discriminate between assays without a compensation algorithm.

Positive Calling Algorithm

Assay discrimination actually takes place as part of the positive calling algorithm that processes the raw data from the optical detection system. The algorithm is designed to preclude false positives while reliably calling true positives. False positives from a simplex assay could result from signal noise or linearly increasing signals. With a duplex assay, false positives can also occur as a result of cross talk from the neighboring assay as discussed above. The algorithm used on the HANAA is a modified slope detection processor.

It relies on the rate of rise in signal level, not the absolute level. The latter can be a function of the initial chemistry, system noise or linear signal drift as opposed to an exponential increase.

All raw signals are essentially normalized to the signal obtained after the tenth cycle. That is, the processed signal data always has a value of 1.0 at cycle ten. Cycle ten is used to avoid any initial signal changes due to effects such as incomplete mixing of the sample solution. It is also early enough to avoid interfering with a true positive. Before normalization, all raw signals are offset by a value equal to the difference between 200 counts and the number of counts recorded on cycle ten. This is done to compensate for differences in background signal from assay to assay or from chamber to chamber. It also has the effect of diluting signals that are very weak.

Due to the normalization, a typical PCR run has the processed signal hovering around 1.0 until the exponential increase is observed, typically near or beyond cycle 20, depending on concentration. To minimize the risk of calling false positives, the positive calling algorithm doesn't start analyzing the data until cycle 12. At that point, it starts comparing the increase in normalized signal from the previous cycle to the current cycle. If the increase exceeds a predefined threshold value (typically 0.02), a hit is recorded for that cycle. If three out of four consecutive cycles record hits, the assay is declared to be positive and the user is alerted. The algorithm is depicted graphically in FIG. 7, with a corresponding data analysis table shown in Table 1 below.

TABLE 1

Analytical depiction of algorithm.
(A hit is recorded when the signal increase is 0.02 or greater.)

| Signal | Increase | Hits |
|---|---|---|
| 1.000 | 0.004 | 0 |
| 1.002 | 0.002 | 0 |
| 0.999 | −0.003 | 0 |
| 1.003 | 0.004 | 0 |
| 1.002 | −0.001 | 0 |
| 1.001 | −0.001 | 0 |
| 1.002 | 0.001 | 0 |
| 1.003 | 0.001 | 0 |
| 1.004 | 0.001 | 0 |
| 1.009 | 0.005 | 0 |
| 1.029 | 0.020 | 1 |
| 1.059 | 0.031 | 1 |
| 1.105 | 0.046 | 1 |
| 1.170 | 0.075 | 1 |

As mentioned earlier, the HANAA doesn't display signal versus cycle during a run. (In part, this is due to the fact that the monochrome display resolution is only 64×128 and up to 8 individual assays can be running simultaneously.) Rather, the display is used to convey information about the robustness of the assay and whether or not it is a positive. As such, the display shows a simple bar chart for each of the 8 assays, where the level of the bar corresponds to the number of hits that have occurred in the last four cycles, from 0 to a maximum of 4. A miss is indicated by lowering the level slightly below an integer value. FIG. 8 shows all the available levels depicted as a sequence. A poor assay would have the bar going up and down during the run from 1 to slightly below 1 to 0, with perhaps an occasional rise to just below the 2 level. The 2 level would only be reached if there were two consecutive hits. When 3 of 4 cycles have hits, the bar becomes shaded and the instrument beeps (optional) to indicate a positive. The maximum shaded level is latched for the duration of the run. Standard positive assays have the bar steadily rise from 1 to 2 to 3 (shaded) to 4 (shaded). The 4 level is used as a further indication of a good assay. If the bar never reaches level 4, then the assay was weak and almost wasn't called positive. If the assay is seen to be weak, the user should consider decreasing the slope threshold.

HANAA Electronics/Control System

The control system consists of one or more master microprocessors, and one or more slave microcontrollers. Both types of processor are programmable while in the circuit, allowing for code expansion/modification without opening the system case. The master processor is an Intel 80386EX running DOS. It has 500 k of RAM a clock/calendar, six serial ports and a 2 Mb Flash disk. This processor provides the user interface, log data to disk, allow editing of thermal profiles, run calibration routines for the chambers and perform data analysis (real-time detection of organisms).

The slave microcontrollers are 8 bit devices compatible with the Intel 8051 series. Each controller has 32 k RAM, and 32 k EEPROM, two Pulse Width Modulated outputs for driving the reaction chamber heaters, binary I/O for controlling the cooling fan, LEDs, and control signals, analog inputs for measuring chamber temperature, battery voltage and current and recording the DNA signal from the PCR process.

Summary of Embodiments

Various embodiments of the invention are described and structural details are shown by the drawings. The detailed description of the various embodiments, together with the general description of the invention, serve to explain the principles of the invention. One embodiment provides a polymerase chain reaction DNA amplification and detection system having a main body and one or more sample chamber modules adapted to contain biological sample volumes. Each of the sample chamber modules has the ability to support a duplex assay. Parallel interrogation ports are operatively connected to the sample chamber modules.

Another embodiment of the polymerase chain reaction DNA amplification and detection includes a linear detection system operatively connected to each of said interrogation ports. The linear detection systems are positioned substantially parallel to each other. The sample chamber modules are removeably connected to the main body. Another embodiment of the polymerase chain reaction DNA amplification and detection system is capable of being handheld. The main body is about 10 inches or less long, about 4 inches or less wide, about 2 inches or less deep, and weighs about 2 pounds or less. Another embodiment of the polymerase chain reaction DNA amplification and detection system is battery operated. Each of the sample chamber modules has multiple ports which interrogate distinct regions within the sample volume. Each of the parallel interrogation ports has its own optical fluorescence detection system.

Another embodiment of the polymerase chain reaction DNA amplification and detection system includes a sleeve reaction chamber having a plurality of grooves in the sleeve for reducing thermal mass and increasing surface area of the sleeve. The plurality of grooves include at least one longitudinally extending groove, at least one radially extending groove, and at least one radially extending groove connected to the longitudinally extending groove to form a passageway there-through.

Another embodiment of the system includes a LED which directs light energy into each of the parallel interrogation ports and bandpass filters are located in each of the parallel interrogation ports. Another embodiment of the polymerase chain reaction DNA amplification and detection system includes a positive calling algorithm, an assay status user interface, one or more master microprocessors, and one or more slave microcontrollers.

In the various embodiments of the system a sample is place in at least one of a multiplicity of sample chamber modules. The sample is heated using a heating unit in a silicon base and the sample is cooled. Light energy is directed into the sample through the parallel interrogation ports and characteristics of the sample are detected.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A polymerase chain reaction DNA amplification and detection system, comprising:
    one or more sample chamber modules for receiving a biological sample,
    each of said sample chamber modules supporting at least two independent measurements on said biological sample, and
    parallel interrogation ports operatively connected to said sample chamber modules.

2. The polymerase chain reaction DNA amplification and detection system of claim 1, including a linear detection system operatively connected to each of said interrogation ports.

3. The polymerase chain reaction DNA amplification and detection system of claim 1, including linear detection systems operatively connected to said interrogation ports, wherein said linear detection systems are positioned extending in the same direction.

4. The polymerase chain reaction DNA amplification and detection system of claim 1, including a main body with said one or more sample chamber modules removeably connected to said main body.

5. The polymerase chain reaction DNA amplification and detection system of claim 4, wherein said main body and said one or more sample chamber modules are capable of being handheld.

6. The polymerase chain reaction DNA amplification and detection system of claim 4, wherein said main body is less than about 12 inches long.

7. The polymerase chain reaction DNA amplification and detection system of claim 4, wherein said main body is about 10 inches or less long.

8. The polymerase chain reaction DNA amplification and detection system of claim 4, wherein said main body is less than about 6 inches wide.

9. The polymerase chain reaction DNA amplification and detection system of claim 4, wherein said main body is about 4 inches or less wide.

10. The polymerase chain reaction DNA amplification and detection system of claim 4, wherein said main body is less than about 4 inches deep.

11. The polymerase chain reaction DNA amplification and detection system of claim 4, wherein said main body is about 2 inches or less deep.

12. The polymerase chain reaction DNA amplification and detection system of claim 4, wherein said main body and said one or more sample chamber modules weigh less than about 5 pounds.

13. The polymerase chain reaction DNA amplification and detection system of claim 4, wherein said main body and said one or more sample chamber modules weigh about 2 pounds or less.

14. The polymerase chain reaction DNA amplification and detection system of claim 4, wherein said main body and said one or more sample chamber modules are battery operated.

15. The polymerase chain reaction DNA amplification and detection system of claim 1, wherein each of said interrogation ports has a unique optical fluorescence detection system.

16. The polymerase chain reaction DNA amplification and detection system of claim 1, wherein each of said parallel interrogation ports has its own optical fluorescence detection system.

17. The polymerase chain reaction DNA amplification and detection system of claim 1, wherein each of said sample chamber modules has multiple ports which interrogate distinct regions within said sample volume using its own optical fluorescence detection system.

18. The polymerase chain reaction DNA amplification and detection system of claim 1, including a sleeve reaction chamber having a plurality of grooves in the sleeve for reducing thermal mass and increasing surface area of the sleeve.

19. The polymerase chain reaction DNA amplification and detection system of claim 18, wherein said plurality of grooves includes at least one longitudinally extending groove, and at least one radially extending groove, and at least one radially extending groove connected to said longitudinally extending groove to form a passageway therethrough.

20. The polymerase chain reaction DNA amplification and detection system of claim 19, wherein said plurality of grooves includes at least one longitudinally extending groove on opposite sides of said sleeve, and at least one radially extending groove connected to each of said longitudinally extending grooves to form passageways therethrough.

21. The polymerase chain reaction DNA amplification and detection system of claim 20, wherein two longitudinally extending grooves are located on opposite sides of said sleeve, and wherein said plurality of connecting radially extending grooves are located along opposite end sections of said sleeve.

22. The polymerase chain reaction DNA amplification and detection system of claim 21, wherein each of said grooves is of a V-shaped configuration.

23. The polymerase chain reaction DNA amplification and detection system of claim 22, wherein said sleeve is constructed of silicon.

24. The polymerase chain reaction DNA amplification and detection system of claim 23, wherein said sleeve reaction chamber is composed of two sections, said sections being bonded or clamped together.

25. The polymerase chain reaction DNA amplification and detection system of claim 24, wherein said two sections are configured to define a chamber to enclose an insert therebetween such that said insert is in direct contract with at least a portion of walls of said two sections defining the chamber.

26. The polymerase chain reaction DNA amplification and detection system of claim 1, wherein an LED directs light energy into each of said parallel interrogation ports.

27. The polymerase chain reaction DNA amplification and detection system of claim 26, including bandpass filters in each of said parallel interrogation ports.

28. The polymerase chain reaction DNA amplification and detection system of claim 1, including a non-orthogonal fluorescence, highly compact optical detection system.

29. The polymerase chain reaction DNA amplification and detection system of claim 1, including an assay status user interface.

30. The polymerase chain reaction DNA amplification and detection system of claim 1, including one or more master microprocessors and one or more slave microcontrollers.

31. The polymerase chain reaction DNA amplification and detection system of claim 1, including a positive calling algorithm for determining when a biological agent was present in said sample volume.

32. The polymerase chain reaction DNA amplification and detection system of claim 1, including a status display that indicates the viability of a particular assay.

33. The polymerase chain reaction DNA amplification and detection system of claim 25, including electronics located in said main body and forced cooling ducts for efficiently coupling external air through said sleeve reaction chamber then out of said main body, thereby cooling said sample and said electronics simultaneously.

34. A method of polymerase chain reaction DNA amplification and detection, comprising the steps of:
   placing a biological sample in a sample chamber module that supports at least two independent measurements on said biological sample, and
   directing light energy into said biological sample through parallel interrogation ports operatively connected to said sample chamber module.

35. The method of polymerase chain reaction DNA amplification and detection of claim 34, wherein said light energy is directed into said biological sample through a linear detection system.

36. The method of polymerase chain reaction DNA amplification and detection of claim 34, including the steps of:
   heating said sample using a heating unit in a silicon base, and
   cooling said sample.

37. The method of polymerase chain reaction DNA amplification and detection of claim 36, including forcing cooling air through a sleeve reaction chamber to cooling said biological sample.

38. The method of polymerase chain reaction DNA amplification and detection of claim 34, wherein said sample chamber module includes an individual sample chamber and including the step of temporarily overheating said sample chamber for the purpose of having said biological sample achieve and hold a desired temperature as rapidly as possible.

39. The method of polymerase chain reaction DNA amplification and detection of claim 34, including the step of:
   determining that an assay of said sample is positive based on a positive calling algorithm.

40. The method of polymerase chain reaction DNA amplification and detection of claim 39, including the step of:
   displaying in real-time the degree of certainty or of reliability for each said assay.

* * * * *